US009545373B2

(12) United States Patent
Lu et al.

(10) Patent No.: US 9,545,373 B2
(45) Date of Patent: Jan. 17, 2017

(54) TRANSLUCENT COSMETIC COMPOSITION IN THE FORM OF A WATER-IN-OIL EMULSION

(71) Applicant: L'OREAL, Paris (FR)

(72) Inventors: Gloria Lu, Rahway, NJ (US); Lauren Elizabeth Manning, Hoboken, NJ (US); Patricia Brieva, Manlapan, NJ (US); Donna McCann, Oxford, NJ (US); Jing Qi, Iselin, NJ (US)

(73) Assignee: L'OREAL, Paris (FR)

( * ) Notice: Subject to any disclaimer, the term of this patent is extended or adjusted under 35 U.S.C. 154(b) by 214 days.

(21) Appl. No.: 14/136,602

(22) Filed: Dec. 20, 2013

(65) Prior Publication Data

US 2015/0174050 A1   Jun. 25, 2015

(51) Int. Cl.
| | |
|---|---|
| A61K 8/893 | (2006.01) |
| A61K 8/42 | (2006.01) |
| A61K 8/49 | (2006.01) |
| A61K 8/365 | (2006.01) |
| A61K 8/58 | (2006.01) |
| A61K 8/67 | (2006.01) |
| A61Q 19/00 | (2006.01) |
| A61K 8/894 | (2006.01) |
| A61K 8/06 | (2006.01) |

(52) U.S. Cl.
CPC ............... *A61K 8/893* (2013.01); *A61K 8/064* (2013.01); *A61K 8/365* (2013.01); *A61K 8/42* (2013.01); *A61K 8/4913* (2013.01); *A61K 8/585* (2013.01); *A61K 8/675* (2013.01); *A61K 8/676* (2013.01); *A61K 8/894* (2013.01); *A61Q 19/00* (2013.01); *A61K 2800/10* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 4,268,499 A | 5/1981 | Keil | |
| 4,917,882 A | 4/1990 | Strobridge | |
| 5,601,811 A | 2/1997 | Gallagher et al. | |
| 6,524,598 B2 | 2/2003 | Sunkiel et al. | |
| 6,555,119 B1 | 4/2003 | Mori et al. | |
| 6,696,049 B2 | 2/2004 | Vatter et al. | |
| 7,262,217 B2 | 8/2007 | Baranger et al. | |
| 8,216,555 B2 | 7/2012 | Nieuwenhuijsen | |
| 8,299,127 B2 | 10/2012 | Anjing et al. | |
| 8,461,206 B2 | 6/2013 | Dalko | |
| 8,481,594 B2 | 7/2013 | Boulle et al. | |
| 8,603,502 B2 | 12/2013 | Boulle et al. | |
| 8,609,117 B2 | 12/2013 | Boulle et al. | |
| 2003/0064046 A1 | 4/2003 | Omura et al. | |
| 2005/0074420 A1* | 4/2005 | Bourdel | A61K 8/06 424/70.12 |
| 2007/0128137 A1 | 6/2007 | Yoshimi et al. | |
| 2007/0264210 A1* | 11/2007 | Robinson | A61K 8/675 424/59 |
| 2009/0011035 A1 | 1/2009 | Zukowski et al. | |
| 2009/0035236 A1 | 2/2009 | Maes et al. | |
| 2010/0129301 A1 | 5/2010 | Tanaka et al. | |
| 2010/0179222 A1 | 7/2010 | Boulle et al. | |
| 2010/0310617 A1 | 12/2010 | Zhang et al. | |
| 2011/0256077 A1 | 10/2011 | Hayakawa | |
| 2012/0088836 A1 | 4/2012 | Dalko | |
| 2012/0322876 A1 | 12/2012 | Kermorvan et al. | |
| 2013/0039961 A1 | 2/2013 | Gonzales et al. | |
| 2013/0142740 A1 | 6/2013 | Cziryak et al. | |
| 2013/0345317 A1 | 12/2013 | Chiou | |

FOREIGN PATENT DOCUMENTS

| | | |
|---|---|---|
| CN | 1793822 A | 6/2008 |
| EP | 1027883 A2 | 8/2000 |
| EP | 1671680 A1 | 6/2006 |
| EP | 1990372 A2 | 11/2008 |
| FR | 2847469 A1 | 5/2004 |
| FR | 2847470 A1 | 5/2004 |
| FR | 288114 A1 * | 1/2007 |
| FR | 2909552 A1 | 6/2008 |

(Continued)

OTHER PUBLICATIONS

U.S. Appl. No. 14/136,471, filed Dec. 20, 2013, Catherine Chiou.
U.S. Appl. No. 14/136,562, filed Dec. 20, 2013, Angelike Galdi.
U.S. Appl. No. 14/136,634, filed Dec. 20, 2013, Catherine Chiou.
U.S. Appl. No. 13/529,059, filed Jun. 21, 2013, Catherine Chiou.
U.S. Appl. No. 13/855,495, filed Apr. 2, 2013, Catherine Chiou.
PCT/US2013/045613, June. 13, 2013, Catherine Chiou.
C. Tran, "In vitro and in vivo studies with tetra-hydro-jasmonic acid (LR2412) reveal its potential to correct signs of skin ageing", Journal of the European Academy of Dermatology and Venereology, DOI 10.1111, 2013, pp. 1-9.

(Continued)

*Primary Examiner* — Qiuwen Mi
(74) *Attorney, Agent, or Firm* — McNees Wallace & Nurick LLC (57) ABSTRACT

A transparent or translucent cosmetic composition in the form of a water-in-oil emulsion is provided. The composition includes an aqueous phase at a concentration, by weight, of about 50%-90%, based upon weight of the composition. The aqueous phase includes at least one amphiphilic compound selected from the group consisting of urea, sodium 5-oxo-2-pyrrolidinecarboxylate (sodium PCA), hydroxyethyl urea, nicotinamide, sodium citrate, ascorbic acid, or combinations thereof. The at least one amphiphilic compound is at a concentration, by weight, of about 2% to about 50%, based upon weight of the composition. The composition includes an oil phase comprising at least one water-in-oil emulsifier at a concentration, by weight, of about 1%-25%, based upon weight of the composition. The water-in-oil emulsion is a transparent or translucent composition.

7 Claims, 2 Drawing Sheets

(56) References Cited

FOREIGN PATENT DOCUMENTS

| FR | 2921254 A1 | 3/2009 |
|---|---|---|
| FR | 2921255 A1 | 3/2009 |
| FR | 2940053 A1 | 6/2010 |
| FR | 2951375 A1 | 4/2011 |
| FR | 2953718 A1 | 6/2011 |
| FR | 2954122 A1 | 6/2011 |
| FR | 2964865 A1 | 3/2012 |
| FR | 2973693 A1 | 10/2012 |
| FR | 2977478 A1 | 1/2013 |
| FR | 2988291 A1 | 9/2013 |
| FR | 2988292 A1 | 9/2013 |
| JP | 2001205061 A | 7/2001 |
| WO | 20000069423 A1 | 11/2000 |
| WO | 2010000584 A2 | 1/2010 |
| WO | 2011054600 A1 | 5/2011 |
| WO | 2012084699 A2 | 6/2012 |
| WO | 2012084701 A2 | 6/2012 |
| WO | 2012136564 A2 | 10/2012 |
| WO | 2012136818 A2 | 10/2012 |
| WO | 2012143645 A2 | 10/2012 |
| WO | 2013007637 A2 | 1/2013 |
| WO | 2013007647 A1 | 1/2013 |

OTHER PUBLICATIONS

M. Vonka, "Modelling the morphology evolution of polymer materials undergoing phase separation", Chemical Engineering Journal, 2012, http//dx.doi.org/10.1016/j.cej.2012.06.091, pp. 1-12.

* cited by examiner

TRANSLUCENT COSMETIC COMPOSITION IN THE FORM OF A WATER-IN-OIL EMULSION

FIELD OF THE INVENTION

The present invention is directed to cosmetic compositions and methods of using and producing cosmetic compositions. More specifically, the present invention is directed to a translucent water-in-oil cosmetic composition including an aqueous phase having at least one amphiphilic compound selected from the group consisting of urea, sodium 5-oxo-2-pyrrolidinecarboxylate (sodium PCA), hydroxyethyl urea, nicotinamide, sodium citrate, ascorbic acid, or combinations thereof, at a concentration, by weight, of about 2% to about 50%, based upon weight of the composition, an active compound, and an oil phase including at least one water-in-oil emulsifier, at a concentration, by weight, of about 1% to about 25%, based upon weight of the composition.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase.

W/O emulsions are often stabilized with silicone elastomeric polymers. Silicone elastomeric polymers may have a nice cosmetic feel but W/O emulsions containing silicone elastomeric polymers are limited in terms of formula robustness and aesthetics.

Emulsions typically appear milky white due to the difference of refractive index between the internal phase and the external phase, leading to scattering of visible light. One approach to creating a translucent or transparent emulsion is to match the refractive index of the two immiscible phases. Generally, to match the refractive index, the refractive difference between the two immiscible phases is only allowed to be about ±0.001-0.005. One drawback of refractive index matching is that the matching requires a large amount of adjusters such as glycols or fluorocarbons, which may result in an undesirable tacky residue or feel when applied to the skin.

Another approach to creating a translucent or transparent emulsion is to reduce the emulsion droplet size such that the emulsion droplet size becomes smaller than one-quarter the wavelength of visible light (generally less than about 100 nm), resulting in a nanoemulsion. Drawbacks of obtaining nanoemulsion include a high cost due to the high energy and high temperatures required for processing to obtain the small droplet size to create the nanoemulsion. Generally heat or increased pressure is required to create nanoemulsions. Process temperature usually exceeds about 75° C., while pressure usually exceeds 1500 bars with at least 7 passages.

Therefore, it is desirable to provide a translucent cosmetic composition in the form of an oil-in water emulsion that has a nice cosmetic feel that does not suffer from one or more of the above drawbacks.

BRIEF DESCRIPTION OF THE INVENTION

In an exemplary embodiment, a cosmetic composition in the form of a water-in-oil emulsion is provided. The cosmetic composition includes an aqueous phase, at least one amphiphilic compound and an oil phase. The aqueous phase is at a concentration, by weight, of about 50% to about 90%, based upon weight of the composition. The aqueous phase includes at least one amphiphilic compound selected from the group consisting of urea, sodium 5-oxo-2-pyrrolidinecarboxylate (sodium PCA), hydroxyethyl urea, nicotinamide, sodium citrate, ascorbic acid, or combinations thereof. The at least one amphiphilic compound is at a concentration, by weight, of about 2% to about 50%, based upon weight of the composition. The oil phase includes at least one water-in-oil emulsifier. The at least one water-in-oil emulsifier is an emulsifying linear silicone at a concentration, by weight, of about 1% to about 25%, based upon weight of the composition. The cosmetic composition is a water-in-oil emulsion and is a transparent or translucent composition.

In another embodiment, a cosmetic composition in the form of a water-in-oil emulsion is provided. The cosmetic composition includes an aqueous phase, at least one amphiphilic compound and an oil phase. The aqueous phase is at a concentration, by weight, of about 50% to about 90%, based upon weight of the composition. The aqueous phase includes at least one amphiphilic compound selected from the group consisting of urea, sodium 5-oxo-2-pyrrolidinecarboxylate (sodium PCA), hydroxyethyl urea, sodium citrate, ascorbic acid, or combinations thereof. The at least one amphiphilic compound is at a concentration, by weight, of about 2% to about 50%, based upon weight of the composition. The oil phase includes at least one water-in-oil emulsifier at a concentration, by weight, of about 1% to about 25%, based upon weight of the composition. The cosmetic composition is a water-in-oil emulsion and is a transparent or translucent composition.

Other features and advantages of the present invention will be apparent from the following more detailed description of the preferred embodiment which illustrates, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

"Keratinous tissue," as used herein, includes but is not limited to skin, hair, and nails.

"Homogenous," as used herein, means substantially uniform throughout, i.e., a single phase mixture.

"Transparency" or "Translucency", as used herein, refers to an appearance of text through the emulsion. Transparency is measured using a chromameter that measures the absolute numbers in the XYZ color spaces. A 0.2 mm film of a sample is drawn down and the luminance, Y, is measured on black and white color tiles. The percent (%) transparency is obtained using the following calculation: $100*(1-(Y_{black}/Y_{white}))$. A percent transparency of greater than about 83% is considered transparent. A percent transparency of less than about 83% is not considered transparent.

In the present application the term "ambient temperature" means a temperature of about 25° C.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventors that a transparent or translucent water-in-oil composition is obtained using a cold process, at low expense without comprising desired consumer sensorial experience. It has also been surprisingly discovered by the inventors that a transparent or translucent water-in-oil composition is obtained without having to use refractive index matching of the two immiscible phases. It has also been surprisingly discovered by the inventors that a transparent or translucent water-in-oil composition is obtained at a low cost. It has also been surprisingly discovered that a transparent or translucent water-in-oil composition has a decreased droplet diameter for the emulsion that is obtainable at ambient temperature without having to use high energy or high temperature processing. It has been surprisingly discovered by the inventors that a transparent or translucent water-in-oil composition is obtained in a dose dependent manner using amphiphilic compounds. It has also been surprisingly discovered by the inventors that the addition of at least one active to a transparent or translucent water-in-oil composition increases the percent transparency.

Provided is a cosmetic composition in the form of a water-in-oil emulsion that includes an aqueous phase, at least one amphiphilic compound and an oil phase. The aqueous phase is at a concentration, by weight, of about 50% to about 90%, based upon weight of the composition. The aqueous phase includes at least one amphiphilic compound selected from the group consisting of urea, sodium 5-oxo-2-pyrrolidinecarboxylate (sodium PCA), hydroxyethyl urea, nicotinamide, sodium citrate, ascorbic acid, or combinations thereof. The at least one amphiphilic compound is at a concentration, by weight, of about 2% to about 50%, based upon weight of the composition. The oil phase includes at least one water-in-oil emulsifier at a concentration, by weight, of about 1% to about 25%, based upon weight of the composition. The water-in-oil emulsion is a transparent or translucent composition.

Aqueous Phase

The aqueous phase present in the cosmetic composition according to the present disclosure includes water, glycerin, and at least one amphiphilic compound. In one embodiment, the aqueous phase comprises, by weight, about 50% to about 90%, or alternatively about 60% to about 90%, or alternatively about 70% to about 85%, based upon weight of the composition. The glycerin is at a concentration, by weight of about 2% to about 20%, or alternatively about 2% to about 15%, or alternatively about 2% to about 10%, based upon weight of the composition.

Amphiphilic Compounds

Amphiphilic compounds are compounds comprising one or more hydrophilic parts that make them partially water-soluble and one or more hydrophobic parts via which associate or interact with an oily phase. The at least one amphiphilic compound present in the cosmetic composition according to the disclosure includes urea, sodium 5-oxo-2-pyrrolidinecarboxylate (sodium PCA), hydroxyethyl urea, nicotinamide, sodium citrate, ascorbic acid, or combinations thereof. In one embodiment, the at least one amphiphilic compound is nicotinamide. The at least one amphiphilic compound is at a concentration, by weight, of about 2% to about 50%, or alternatively about 2% to about 20%, or alternatively about 5% to about 20%, or alternatively about 2% to about 15%, or alternatively about 4% to about 12%, or alternatively about 5% to about 12%, based upon weight of the composition. In one embodiment, the amphiphilic compound is nicotinamide at a concentration, by weight, of about 2% to about 20%, or alternatively about 4% to about 12%, or alternatively about 5% to about 12%, based upon weight of the composition.

Active Compound

In one embodiment, the aqueous phase includes at least one active compound. In another embodiment, the at least one active compound is at a concentration, by weight, of about 0.001% to about 30%, or alternatively about 0.001% to about 20%, or alternatively about 0.001% to about 10%, based upon weight of the composition. In another embodiment, the active compound is an anti-aging compound, an ultraviolet (UV) active compound, an anti-acne compound, an anti-perspiration compound, an anti-pigmentation compound, an anti-inflammation compound, an antioxidant (e.g., EDTA, BHT, tocopherol), or a combination thereof. Suitable examples of active compounds include, but are not limited to, caffeine, adenosine, *scutellaria baicalensis* root extract, resveratrol, tocopherol, hydroxypropyl tetrahydropyrantriol, terephthalylidene dicamphor sulfonic acid, and combinations thereof.

Other examples of active compounds include, but are not limited to, sunscreen agents, free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, -hydroxy acids and mixtures thereof, and enhancing agents.

In one embodiment, the cosmetic composition may optionally include a preservative. Suitable examples of preservatives include, but are not limited to, phenoxyethanol, ethylhexylglycerin, chlorphenesin. In one embodiment, the chelating agent is at a concentration, by weight, of about 0.05% to about 0.70%, or alternatively about 0.06% to about 0.40%, or alternatively about 0.1% to about 0.3%, based upon weight of the composition.

The aqueous phase may also contain cosmetically acceptable additives or adjuvants as well as cosmetic or dermatologic active agents. Representative additives and adjuvants include, for example, water-soluble or water-miscible solvents or co-solvents, humectants, moisturizers, colorants, fillers, essential oils, fragrances, dyes, neutralizing or pH-adjusting agents (e.g., triethylamine (TEA) and sodium hydroxide), conditioning or softening agents (e.g., panthenol, allantoin and glycerin) and extracts such as botanical extracts. Additives and adjuvants may be present in the compositions in amounts generally ranging from about 0.01% to about 10% by weight.

Oil Phase

The oil phase present in the composition according to the disclosure includes a silicone oil and at least one water-in-oil emulsifier. In one embodiment, the oil phase is at a concentration of about 10% to about 50%, or alternatively about 15% to about 40%, or alternatively about 15% to about 30%, based upon weight of the composition.

The oil phase of the present disclosure includes silicone oils which are excellent alternatives for traditional oils that are frequently used in personal care formulations. The use of formulations containing traditional oils often leaves the user the impression of greasiness, tackiness, oiliness, or coating. Silicone oils on the other hand, have the benefits of traditional oils, but lack the unfavorable properties and leave a tactile impression of softness, smoothness, and lightness. Non-volatile as well as volatile silicone oils may be used. Non-volatile silicones provide a lasting tactile impression, and tend to form a stable oil layer on the skin. If desired, volatile silicones may be used in combination with non-volatile silicones to impart desired esthetic properties, but preferably the emulsions should contain sufficient non-volatile silicone to provide a skin barrier layer.

Particularly suitable examples of silicone oils, include, but are not limited to dimethicone, dimethicone (and) dimethiconol, or combinations thereof. In one embodiment, the silicone oils includes co-emulsifiers, such as, but not limited to, lauryl PEG-9 polydimethylsiloxyethyl dimethicone, PEG-10 dimethicone, PEG-9 polydimethylsiloxyethyl dimethicone (and) PEG-9. The co-emulsifiers facilitate stability of the composition. In another embodiment, the oil phase may also include cosmetically acceptable additives or adjuvants as well as cosmetic or dermatologic active agents.

Water-in-Oil Emulsifier

The water-in-oil emulsifier present in the cosmetic composition may be a self-emulsifying silicone elastomer. The self-emulsifying silicone elastomer may include functional groups selected from the group consisting of polyglyceryl, polyethylene glycol, or polypropylene glycol. The at least one water-in-oil emulsifier is selected from the group consisting of dimethicone (and) dimethicone/PEG-10/15 crosspolymer, dimethicone (and) PEG/PPG-18/18 dimethicone, cyclopentasiloxane (and) PEG/PPG-18/18 dimethicone, dimethicone (and) dimethicone/polyglycerin-3 crosspolymer, or combinations thereof.

The water-in-oil emulsifier is advantageously present at a concentration of about 1% to about 25%, or alternatively about 3% to about 10%, or alternatively about 5% to about 8%, by weight, based upon weight of the composition.

Suitable examples of commercially available water-in-oil emulsifiers, include, but are not limited to, dimethicone and dimethicone/PEG-10/15 crosspolymer, under the tradename KSG-210, dimethicone (and) dimethicone/polyglycerin-3 crosspolymer, under the tradename of KSG-710, dimethicone (and) PEG/PPG-18/18 dimethicone, under the tradename X-22-6711D, all three available from Shin-Etsu Silicones of America, Inc., Akron, Ohio, cyclopentasiloxane (and) PEG/PPG-18/18 dimethicone under the tradename of Dow Corning® 5225C formulation aid, available from Dow Corning Corporation, Midland, Mich.

In one embodiment, the oil phase comprising at least one water-in-oil emulsifier, the water-in-oil emulsifier being an emulsifying linear silicone at a concentration, by weight, of about 1% to about 25%, or alternatively about 3% to about 10%, or alternatively about 5% to about 8%, based upon weight of the composition. In one embodiment, the emulsifying linear silicone is dimethicone (and) PEG/PPG-18/18 dimethicone.

Additional Solvents

In one embodiment, the composition includes at least one additional solvent. In another embodiment, the at least one additional solvent is at a concentration, by weight, of about 0.01% to about 30%, or alternatively about 0.01% to about 20%, or alternatively about 0.01% to about 10%, or alternatively about 0.01% to about 5%, based upon weight of the composition. Suitable examples of additional solvents include, but are not limited to, propylene glycol, dipropylene glycol, alcohol denat., and combination thereof. In one embodiment, the at least one additional solvent is included to facilitate incorporation of the at least one active compound. For example, in another embodiment, the at least one additional solvent is included to facilitate incorporation of resveratrol, tocopherol, or a combination thereof.

Transparency/Translucency

Figure 1:
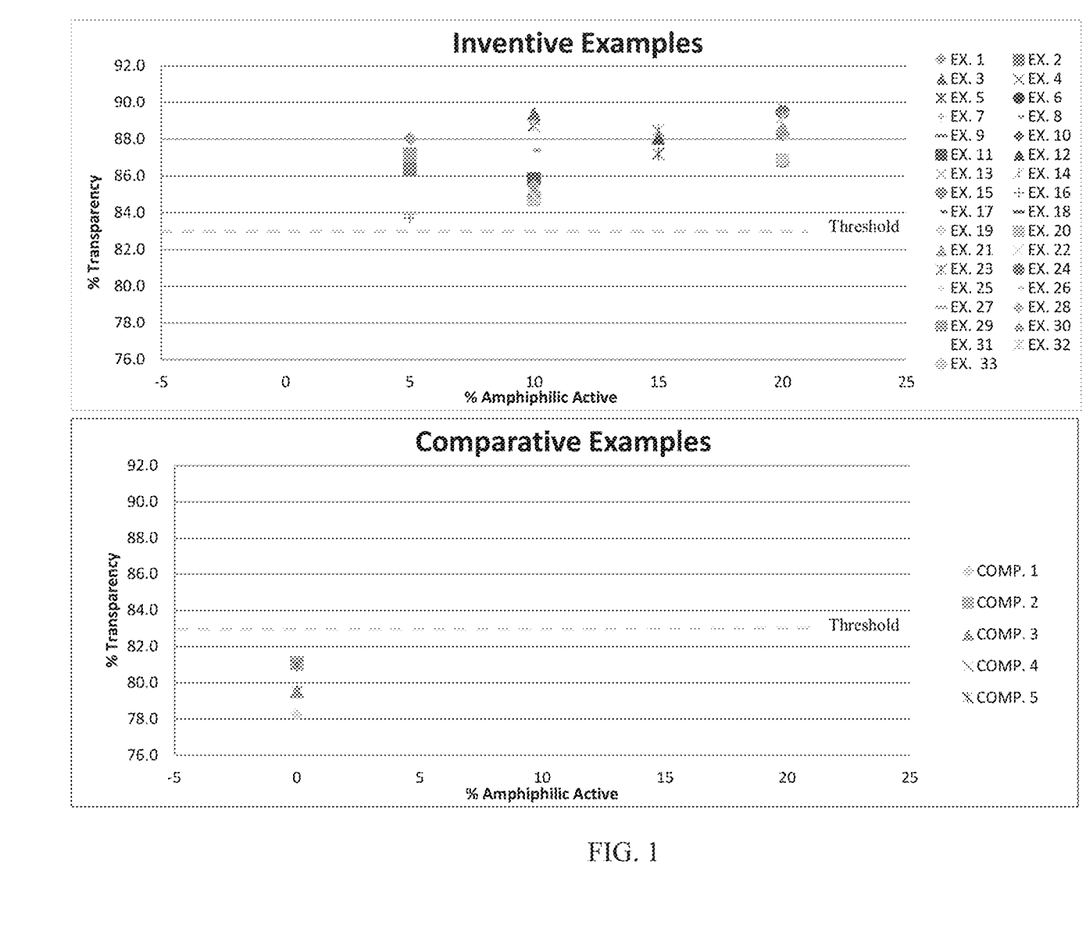
FIG. 1 shows a comparison of average percent (%) transparency of the Comparative Examples versus the Inventive Examples including amphiphilic compounds according to the present disclosure.

The water-in-oil emulsions of the present disclosure are transparent or translucent, as shown in Examples 1-33 and also shown in FIG. 1. As shown in these examples, the transparency or translucency of the water-in-oil emulsions provides the appearance of text through the composition. For each of the Inventive Examples in Table 2, the transparency is measured using a chromameter such as the Spectramagic NX Chromameter available from Konica Minolta Sensing Americas, Inc. (Ramsey, N.J.). The chromameter measures the absolute numbers in the XYZ color spaces. To measure the transparency, a 0.2 mm film of a sample is drawn down on a 50 μm thick polyethylene substrate, for example, and the luminance, Y, is measured on black and white color tiles. The percent (%) transparency is obtained using the measured Yblack and Ywhite value and the following formula: $100*(1-(Yblack/Ywhite))$. A percent transparency of greater than about 83% is considered transparent. A percent transparency of less than about 83% is not considered transparent. Inventive Examples 1-33 all have a percent transparency of greater than about 83% and are transparent, this is further illustrated in FIG. 1. The Comparative Examples, Comp. 1-Comp. 5 have a percent transparency of less than 81%, which is less than the 83% threshold and are not transparent, instead are opaque. It is noted that even minor differences in transparency, for example about 0.8% transparency, as measured by the chromameter, are perceivable by the human eye.

The method for treating keratinous tissue includes applying to the keratinous tissue the cosmetic composition of the present disclosure. The water-in-oil emulsions obtained using the compositions of the present disclosure are suitable for applications to keratinous tissue in the form of, such as, but not limited to, skincare lotions, skin care gels, and skin care creams.

The process of preparing the water-in-oil emulsion of the present disclosure includes mixing the aqueous phase at ambient temperature. The process includes separately mixing the oil phase at ambient temperature. The process then includes slowly adding the mixed aqueous phase to the mixed oil phase while mixing in a container and homogenizing to form a translucent water-in-oil emulsion at ambient temperature.

EXAMPLES

TABLE 1

| | | Comparative Examples | | | | |
|---|---|---|---|---|---|---|
| Phase | INCI Name | COMP. 1 | COMP. 2 | COMP. 3 | COMP. 4 | COMP. 5 |
| A | DIMETHICONE | 15.5 | 15.5 | — | 13 | 13 |
| A | LAURYL PEG-9 POLYDIMETHYLSILOXYETHYL DIMETHICONE | — | — | 3 | | |

TABLE 1-continued

Comparative Examples

| Phase | INCI Name | COMP. 1 | COMP. 2 | COMP. 3 | COMP. 4 | COMP. 5 |
|---|---|---|---|---|---|---|
| A | PEG-10 DIMETHICONE | — | — | — | 2 | 2 |
| A | DIMETHICONE | — | — | 13 | — | — |
| A | DIMETHICONE (and) DIMETHICONOL | — | — | 2 | — | — |
| A | DIMETHICONE (and) PEG/PPG-18/18 DIMETHICONE [X-22] | 7 | 7 | — | — | — |
| A | DIMETHICONE (and) DIMETHICONE/POLYGLYCERIN-3 CROSSPOLYMER [KSG-710] | — | — | — | — | 5 |
| A | DIMETHICONE (and) DIMETHICONE/PEG-10/15 CROSSPOLYMER [KSG-210] | — | — | — | 5 | 5 |
| B | WATER | 49.95 | 51.4 | 60.8 | 70.3 | 70.3 |
| B | DISODIUM EDTA | 0.1 | 0.1 | — | — | — |
| B | SODIUM CHLORIDE | 2 | 2 | — | 0.4 | 0.4 |
| B | SCUTELLARIA BAICALENSIS ROOT EXTRACT | 0.2 | — | — | — | — |
| B | GLYCERIN | 3 | 3 | — | 3 | 3 |
| B | TEREPHTHALYLIDENE DICAMPHOR SULFONIC ACID | — | — | 9 | — | — |
| B | TRIETHANOLAMINE | — | — | 1.8 | — | — |
| B | HYDROXYPROPYL TETRAHYDROPYRANTRIOL | — | — | 3.15 | 3.15 | 3.15 |
| C | PROPYLENE GLYCOL | 9 | 9 | 2.25 | 3.15 | 3.15 |
| C | DIPROPYLENE GLYCOL | 7 | 7 | — | — | — |
| C | RESVERATROL | 0.25 | — | — | — | — |
| C | ALCOHOL DENAT. | 5 | 5 | — | — | — |
| C | TOCOPHEROL | 1 | — | — | — | — |
| | Total (wt/wt %) | 100 | 100 | 100 | 100 | 100 |
| | Average % Transparency | 78.3 | 81.1 | 79.5 | 79.5 | 81.0 |

TABLE 2

| Phase | INCI Name | EX. 1 | EX. 2 | EX. 3 | EX. 4 | EX. 5 | EX. 6 |
|---|---|---|---|---|---|---|---|
| A | DIMETHICONE | 15.5 | 15.5 | 15.5 | 15.5 | 15.5 | 15.5 |
| A | LAURYL PEG-9 POLYDIMETHYLSILOXYETHYL DIMETHICONE | — | — | — | — | — | — |
| A | PEG-10 DIMETHICONE | — | — | — | — | — | — |
| A | DIMETHICONE | — | — | — | — | — | — |
| A | DIMETHICONE (and) DIMETHICONOL | — | — | — | — | — | — |
| A | DIMETHICONE (and) PEG/PPG-18/18 DIMETHICONE [X-22] | 7 | 7 | 7 | 7 | 7 | 7 |
| A | DIMETHICONE (and) DIMETHICONE/POLYGLYCERIN-3 CROSSPOLYMER [KSG-710] | — | — | — | — | — | — |
| A | DIMETHICONE (and) DIMETHICONE/PEG-10/15 CROSSPOLYMER [KSG-210] | — | — | — | — | — | — |
| B | WATER | 41.9 | 46.4 | 41.4 | 41.4 | 36.4 | 31.4 |
| B | DISODIUM EDTA | 0.1 | 0.1 | 0.1 | 0.1 | 0.1 | 0.1 |
| B | SODIUM CHLORIDE | 2 | 2 | 2 | 2 | 2 | 2 |
| B | NIACINAMIDE | 5 | 5 | 10 | — | — | — |
| B | UREA | — | — | — | — | — | 20 |
| B | HYDROXYETHYL UREA | — | — | — | — | 15 | — |
| B | ASCORBIC ACID | — | — | — | 10 | — | — |
| B | SODIUM PCA | — | — | — | — | — | — |
| B | SODIUM CITRATE | — | — | — | — | — | — |
| B | CAFFEINE | 2 | — | — | — | — | — |
| B | SCUTELLARIA BAICALENSIS ROOT EXTRACT | 0.5 | — | — | — | — | — |
| B | GLYCERIN | 3 | 3 | 3 | 3 | 3 | 3 |
| B | TEREPHTHALYLIDENE DICAMPHOR SULFONIC ACID | — | — | — | — | — | — |
| B | TRIETHANOLAMINE | — | — | — | — | — | — |
| B | HYDROXYPROPYL TETRAHYDROPYRANTRIOL | — | — | — | — | — | — |
| C | PROPYLENE GLYCOL | 9 | 9 | 9 | 9 | 9 | 9 |
| C | DIPROPYLENE GLYCOL | 7 | 7 | 7 | 7 | 7 | 7 |
| C | RESVERATROL | 1 | — | — | — | — | — |

TABLE 2-continued

| Phase | INCI Name | | | | | | |
|---|---|---|---|---|---|---|---|
| C | ALCOHOL DENAT. | 5 | 5 | 5 | 5 | 5 | 5 |
| C | TOCOPHEROL | 1 | — | — | — | — | — |
| | Total (wt/wt %) | 100 | 100 | 100 | 100 | 100 | 100 |
| | Average % Transparency | 88.0 | 86.4 | 89.4 | 88.7 | 87.2 | 86.8 |

| Phase | INCI Name | EX. 7 | EX. 8 | EX. 9 | EX. 10 | EX. 11 | EX. 12 |
|---|---|---|---|---|---|---|---|
| A | DIMETHICONE | 15.5 | 15.5 | — | — | — | — |
| A | LAURYL PEG-9 POLYDIMETHYLSILOXYETHYL DIMETHICONE | — | — | 3 | 3 | 3 | — |
| A | PEG-10 DIMETHICONE | — | — | — | — | — | 5 |
| A | DIMETHICONE | — | — | 13 | 13 | 13 | 13 |
| A | DIMETHICONE (and) DIMETHICONOL | — | — | 2 | 2 | 2 | — |
| A | DIMETHICONE (and) PEG/PPG-18/18 DIMETHICONE [X-22] | 7 | 7 | — | — | — | — |
| A | DIMETHICONE (and) DIMETHICONE/POLYGLYCERIN-3 CROSSPOLYMER [KSG-710] | — | — | — | — | — | — |
| A | DIMETHICONE (and) DIMETHICONE/PEG-10/15 CROSSPOLYMER [KSG-210] | — | — | 5 | 5 | 5 | 5 |
| B | WATER | 41.4 | 40.4 | 46.8 | 46.8 | 56.8 | 53.2 |
| B | DISODIUM EDTA | 0.1 | 0.1 | — | — | — | — |
| B | SODIUM CHLORIDE | 2 | 2 | — | — | — | 0.4 |
| B | NIACINAMIDE | — | — | — | — | — | — |
| B | UREA | — | — | 20 | — | — | — |
| B | HYDROXYETHYL UREA | — | — | — | 20 | — | 15 |
| B | ASCORBIC ACID | — | — | — | — | 10 | — |
| B | SODIUM PCA | 10 | — | — | — | — | — |
| B | SODIUM CITRATE | — | 10 | — | — | — | — |
| B | CAFFEINE | — | — | — | — | — | — |
| B | SCUTELLARIA BAICALENSIS ROOT EXTRACT | — | — | — | — | — | — |
| B | GLYCERIN | 3 | 3 | — | — | — | 3 |
| B | TEREPHTHALYLIDENE DICAMPHOR SULFONIC ACID | — | — | 3 | 3 | 3 | — |
| B | TRIETHANOLAMINE | — | — | 1.8 | 1.8 | 1.8 | — |
| B | HYDROXYPROPYL TETRAHYDROPYRANTRIOL | — | — | 3.15 | 3.15 | 3.15 | 3.15 |
| C | PROPYLENE GLYCOL | 9 | 9 | 2.25 | 2.25 | 2.25 | 2.25 |
| C | DIPROPYLENE GLYCOL | 7 | 7 | — | — | — | — |
| C | RESVERATROL | — | — | — | — | — | — |
| C | ALCOHOL DENAT. | 5 | 5 | — | — | — | — |
| C | TOCOPHEROL | — | 1 | — | — | — | — |
| | Total (wt/wt %) | 100 | 100 | 100 | 100 | 100 | 100 |
| | Average % Transparency | 88.8 | 87.4 | 89.5 | 88.4 | 85.8 | 88.1 |

| Phase | INCI Name | EX. 13 | EX. 14 | EX. 15 | EX. 16 | EX. 17 | EX. 18 |
|---|---|---|---|---|---|---|---|
| A | DIMETHICONE | — | — | — | — | — | — |
| A | LAURYL PEG-9 POLYDIMETHYLSILOXYETHYL DIMETHICONE | — | — | — | — | — | — |
| A | PEG-10 DIMETHICONE | 5 | 5 | 5 | 5 | 5 | 5 |
| A | DIMETHICONE | 13 | 13 | 13 | 13 | 13 | 13 |
| A | DIMETHICONE (and) DIMETHICONOL | — | — | — | — | — | — |
| A | DIMETHICONE (and) PEG/PPG-18/18 DIMETHICONE [X-22] | — | — | — | — | — | — |
| A | DIMETHICONE (and) DIMETHICONE/POLYGLYCERIN-3 CROSSPOLYMER [KSG-710] | — | — | — | — | — | — |
| A | DIMETHICONE (and) DIMETHICONE/PEG-10/15 CROSSPOLYMER [KSG-210] | 5 | 5 | 5 | 5 | 5 | 5 |
| B | WATER | 48.2 | 58.2 | 48.2 | 63.2 | 58.2 | 53.2 |
| B | DISODIUM EDTA | 13 | — | — | — | — | — |
| B | SODIUM CHLORIDE | 0.4 | 0.4 | 0.4 | 0.4 | 0.4 | 0.4 |
| B | NIACINAMIDE | — | — | — | — | — | — |
| B | UREA | — | 10 | 20 | | | |
| B | HYDROXYETHYL UREA | 20 | | | | | |
| B | ASCORBIC ACID | — | — | — | — | — | 15 |
| B | SODIUM PCA | | | | 5 | 10 | |
| B | SODIUM CITRATE | | | | | | |

TABLE 2-continued

| Phase | INCI Name | | | | | | |
|---|---|---|---|---|---|---|---|
| B | CAFFEINE | — | — | — | — | — | — |
| B | SCUTELLARIA BAICALENSIS ROOT EXTRACT | — | — | — | — | — | — |
| B | GLYCERIN | 3 | 3 | 3 | 3 | 3 | 3 |
| B | TEREPHTHALYLIDENE DICAMPHOR SULFONIC ACID | — | — | — | — | — | — |
| B | TRIETHANOLAMINE | — | — | — | — | — | — |
| B | HYDROXYPROPYL TETRAHYDROPYRANTRIOL | 3.15 | 3.15 | 3.15 | 3.15 | 3.15 | 3.15 |
| C | PROPYLENE GLYCOL | 2.25 | 2.25 | 2.25 | 2.25 | 2.25 | 2.25 |
| C | DIPROPYLENE GLYCOL | — | — | — | — | — | — |
| C | RESVERATROL | — | — | — | — | — | — |
| C | ALCOHOL DENAT. | — | — | — | — | — | — |
| C | TOCOPHEROL | — | — | — | — | — | — |
| | Total (wt/wt %) | 100 | 100 | 100 | 100 | 100 | 100 |
| | Average % Transparency | 89.7 | 85.2 | 88.3 | 83.7 | 85.1 | 87.4 |

| Phase | INCI Name | EX. 19 | EX. 20 | EX. 21 | EX. 22 | EX. 23 | EX. 24 |
|---|---|---|---|---|---|---|---|
| A | DIMETHICONE | — | — | — | — | — | — |
| A | LAURYL PEG-9 POLYDIMETHYLSILOXYETHYL DIMETHICONE | — | — | — | — | — | — |
| A | PEG-10 DIMETHICONE | 5 | 5 | 5 | 5 | 5 | 5 |
| A | DIMETHICONE | 13 | 13 | 13 | 13 | 13 | 13 |
| A | DIMETHICONE (and) DIMETHICONOL | — | — | — | — | — | — |
| A | DIMETHICONE (and) PEG/PPG-18/18 DIMETHICONE [X-22] | — | — | — | — | — | — |
| A | DIMETHICONE (and) DIMETHICONE/POLYGLYCERIN-3 CROSSPOLYMER [KSG-710] | — | — | — | — | 5 | 5 |
| A | DIMETHICONE (and) DIMETHICONE/PEG-10/15 CROSSPOLYMER [KSG-210] | 5 | 5 | 5 | 5 | — | — |
| B | WATER | 58.2 | 58.2 | 48.2 | 56.6 | 53.2 | 48.2 |
| B | DISODIUM EDTA | — | — | — | — | — | — |
| B | SODIUM CHLORIDE | 0.4 | 0.4 | 0.4 | 0.4 | 0.4 | 0.4 |
| B | NIACINAMIDE | — | — | — | — | — | — |
| B | UREA | — | — | — | — | — | — |
| B | HYDROXYETHYL UREA | | | | | 15 | 20 |
| B | ASCORBIC ACID | 10 | | | — | — | — |
| B | SODIUM PCA | | | | 20 | | |
| B | SODIUM CITRATE | | 10 | 20 | | | |
| B | CAFFEINE | — | — | — | — | — | — |
| B | SCUTELLARIA BAICALENSIS ROOT EXTRACT | — | — | — | — | — | — |
| B | GLYCERIN | 3 | 3 | 3 | | 3 | 3 |
| B | TEREPHTHALYLIDENE DICAMPHOR SULFONIC ACID | — | — | — | — | — | — |
| B | TRIETHANOLAMINE | — | — | — | — | — | — |
| B | HYDROXYPROPYL TETRAHYDROPYRANTRIOL | 3.15 | 3.15 | 3.15 | — | 3.15 | 3.15 |
| C | PROPYLENE GLYCOL | 2.25 | 2.25 | 2.25 | — | 2.25 | 2.25 |
| C | DIPROPYLENE GLYCOL | — | — | — | — | — | — |
| C | RESVERATROL | — | — | — | — | — | — |
| C | ALCOHOL DENAT. | — | — | — | — | — | — |
| C | TOCOPHEROL | — | — | — | — | — | — |
| | Total (wt/wt %) | 100 | 100 | 100 | 100 | 100 | 100 |
| | Average % Transparency | 84.9 | 84.7 | 88.7 | 86.9 | 88.5 | 89.5 |

| Phase | INCI Name | EX. 25 | EX. 26 | EX. 27 | EX. 28 | EX. 29 | EX. 30 |
|---|---|---|---|---|---|---|---|
| A | DIMETHICONE | — | — | — | — | — | — |
| A | LAURYL PEG-9 POLYDIMETHYLSILOXYETHYL DIMETHICONE | — | — | — | — | — | — |
| A | PEG-10 DIMETHICONE | 5 | 5 | 5 | 5 | 5 | 5 |
| A | DIMETHICONE | 13 | 13 | 13 | 13 | 13 | 13 |
| A | DIMETHICONE (and) DIMETHICONOL | | | | | | |
| A | DIMETHICONE (and) PEG/PPG-18/18 DIMETHICONE [X-22] | — | — | — | — | — | — |
| A | DIMETHICONE (and) DIMETHICONE/POLYGLYCERIN-3 CROSSPOLYMER [KSG-710] | 5 | 5 | 5 | 5 | 5 | 5 |

TABLE 2-continued

| Phase | INCI Name | | | | | | |
|---|---|---|---|---|---|---|---|
| A | DIMETHICONE (and) DIMETHICONE/PEG-10/15 CROSSPOLYMER [KSG-210] | — | — | — | — | — | — |
| B | WATER | 58.2 | 48.2 | 63.2 | 58.2 | 53.2 | 58.2 |
| B | DISODIUM EDTA | — | — | — | — | — | — |
| B | SODIUM CHLORIDE | 0.4 | 0.4 | 0.4 | 0.4 | 0.4 | 0.4 |
| B | NIACINAMIDE | — | — | — | — | — | — |
| B | UREA | 10 | 20 | | | | |
| B | HYDROXYETHYL UREA | | | | | | |
| B | ASCORBIC ACID | — | — | — | — | 15 | 10 |
| B | SODIUM PCA | | | 5 | 10 | | |
| B | SODIUM CITRATE | | | | | | |
| B | CAFFEINE | — | — | — | — | — | — |
| B | *SCUTELLARIA BAICALENSIS* ROOT EXTRACT | — | — | — | — | — | — |
| B | GLYCERIN | 3 | 3 | 3 | 3 | 3 | 3 |
| B | TEREPHTHALYLIDENE DICAMPHOR SULFONIC ACID | — | — | — | — | — | — |
| B | TRIETHANOLAMINE | | | | | | |
| B | HYDROXYPROPYL TETRAHYDROPYRANTRIOL | 3.15 | 3.15 | 3.15 | 3.15 | 3.15 | 3.15 |
| C | PROPYLENE GLYCOL | 2.25 | 2.25 | 2.25 | 2.25 | 2.25 | 2.25 |
| C | DIPROPYLENE GLYCOL | — | — | — | — | — | — |
| C | RESVERATROL | — | — | — | — | — | — |
| C | ALCOHOL DENAT. | — | — | — | — | — | — |
| C | TOCOPHEROL | — | — | — | — | — | — |
| | Total (wt/wt %) | 100 | 100 | 100 | 100 | 100 | 100 |
| | Average % Transparency | 84.6 | 88.1 | 84.0 | 85.5 | 87.1 | 85.2 |

| Phase | INCI Name | EX. 31 | EX. 32 | EX. 33 |
|---|---|---|---|---|
| A | DIMETHICONE | — | — | — |
| A | LAURYL PEG-9 POLYDIMETHYLSILOXYETHYL DIMETHICONE | — | — | — |
| A | PEG-10 DIMETHICONE | 5 | 5 | 5 |
| A | DIMETHICONE | 13 | 13 | 13 |
| A | DIMETHICONE (and) DIMETHICONOL | | | |
| A | DIMETHICONE (and) PEG/PPG-18/18 DIMETHICONE [X-22] | — | — | — |
| A | DIMETHICONE (and) DIMETHICONE/POLYGLYCERIN-3 CROSSPOLYMER [KSG-710] | 5 | 5 | 5 |
| A | DIMETHICONE (and) DIMETHICONE/PEG-10/15 CROSSPOLYMER [KSG-210] | — | — | — |
| B | WATER | 58.2 | 48.2 | 56.6 |
| B | DISODIUM EDTA | — | — | — |
| B | SODIUM CHLORIDE | 0.4 | 0.4 | 0.4 |
| B | NIACINAMIDE | — | — | — |
| B | UREA | | | |
| B | HYDROXYETHYL UREA | | | |
| B | ASCORBIC ACID | | | — |
| B | SODIUM PCA | | | 20 |
| B | SODIUM CITRATE | 10 | 20 | |
| B | CAFFEINE | — | — | — |
| B | *SCUTELLARIA BAICALENSIS* ROOT EXTRACT | — | — | — |
| B | GLYCERIN | 3 | 3 | |
| B | TEREPHTHALYLIDENE DICAMPHOR SULFONIC ACID | — | — | — |
| B | TRIETHANOLAMINE | — | — | — |
| B | HYDROXYPROPYL TETRAHYDROPYRANTRIOL | 3.15 | 3.15 | — |
| C | PROPYLENE GLYCOL | 2.25 | 2.25 | — |
| C | DIPROPYLENE GLYCOL | — | — | — |
| C | RESVERATROL | — | — | — |
| C | ALCOHOL DENAT. | — | — | — |
| C | TOCOPHEROL | — | — | — |
| | Total (wt/wt %) | 100 | 100 | 100 |
| | Average % Transparency | 84.9 | 89.2 | 86.9 |

Procedure

The process for preparing the formulations including dimethicone (and) PEG/PPG-18/18 dimethicone as the water-in-oil emulsifier (Comparative Examples, Comp. 1 and Comp. 2, and Inventive Examples 1-8), includes adding phase A (oil phase) ingredients to a main vessel and mixing with a homogenizer at ambient temperature. In a separate vessel, phase B (aqueous phase) ingredients are mixed at ambient temperature with a propeller mixer until all solids are completely dissolved. Next, the pH of phase B is adjusted to the desired pH. Phase B (aqueous phase) is then slowly added to phase A (oil phase) using a mixer to emulsify and uniformly mix. Phase C, if present, is mixed in a separate side vessel until the at least one active compound is completely dissolved in the at least one additional solvent. Phase C, if present, is then gradually added to the main vessel while mixing. During mixing no additional heat is added to the process and mixing occurs at ambient temperature until a uniform emulsion forms.

The process for preparing the formulations including dimethicone (and) dimethicone/PEG-10/15 or dimethicone (and) dimethicone/polyglycerin-3 crosspolymer as the water-in-oil emulsifier (Comparative Examples 3-5 and Inventive Examples 9-33), includes adding the phase B (aqueous phase) ingredients to a side beaker and mixing well using a stir bar until homogeneous. Phase A (oil phase) ingredients are combined in a main beaker and are mixed well with a propeller mixer (at about 300-700 RPM) and are set aside. Next, the contents of the side beaker containing the homogenized phase B ingredients (aqueous phase) are added to the main beaker and are stirred using a propeller mixer at about 300-700 RPM until the viscosity increases, then the mixing speed is increased to about 700 RPM to about 1200 RPM until the phases are homogenized. Phase C, if present, is mixed in a separate side vessel until the at least one active compound is completely dissolved in the at least one additional solvent. Phase C, if present, is then gradually added to the main vessel while mixing. During mixing no additional heat is added and mixing occurs at ambient temperature until a uniform emulsion forms.

The water-in-oil compositions of the present disclosure surprisingly result in a transparent or translucent emulsion without using refractive index matching. Additionally, the water-in-oil compositions of the present disclosure surprisingly resulting in a transparent or translucent emulsion without having to use additional heat or energy to form nanoemulsions. As shown in Table 2 and FIG. 1, Inventive Examples 1-33 all have an average % transparency value of greater than about 83%, which is generally considered the threshold for transparency. More specifically, Inventive Examples 1-33 have an average % transparency value of greater than about 85%. In contrast, as shown in Table 1 and FIG. 1, Comparative Examples have an average % transparency of about 81% or less and are opaque (see FIG. 2).

Figure 2:
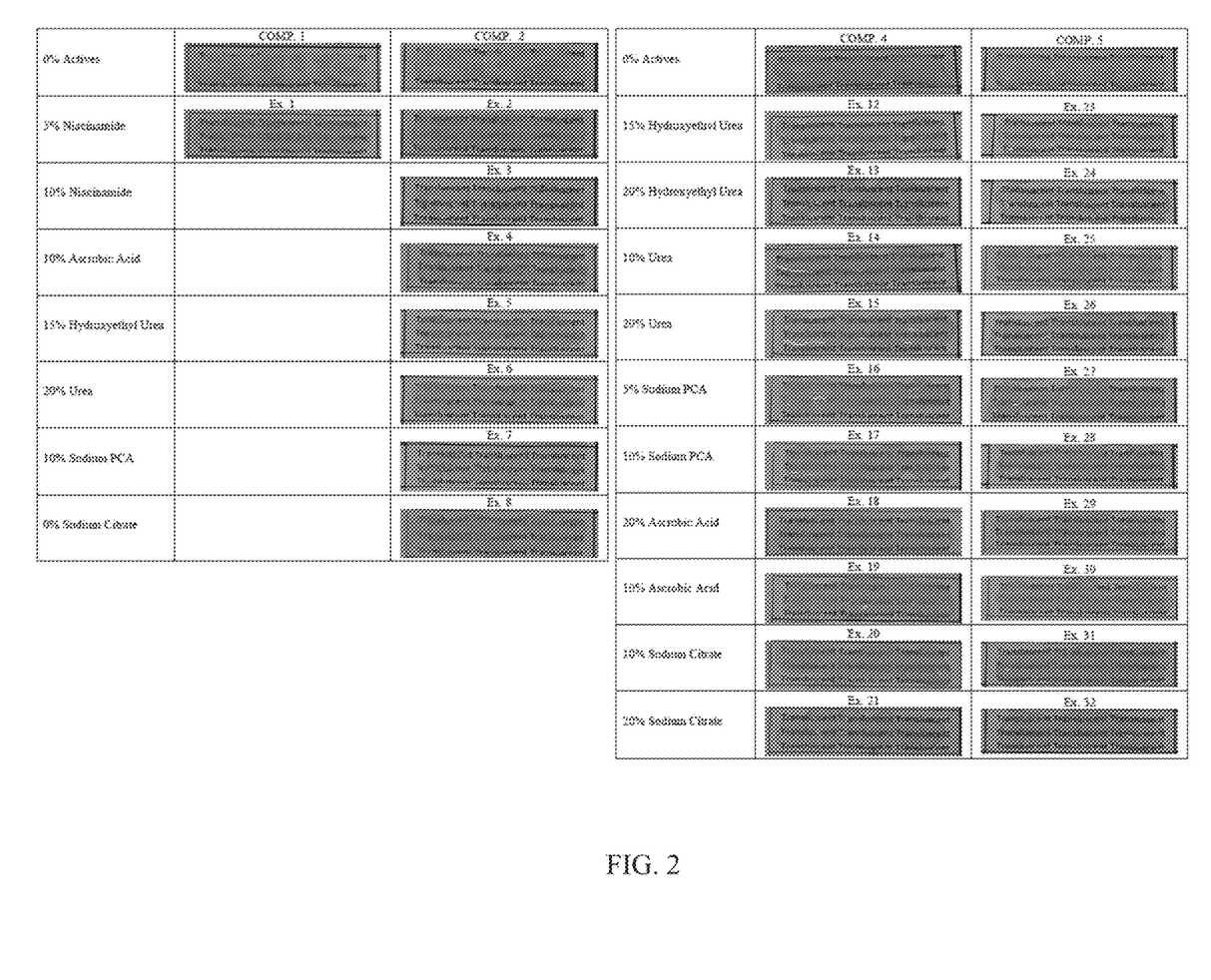
FIG. 2 includes photographs of the opaque Comparative Examples and the transparent Inventive Examples illustrating appearance of text through the composition according to the present disclosure.

FIG. 2 further illustrates the visible difference in transparency of Inventive Examples as compared to the Comparative Examples. In FIG. 2, the compositions obtained from Inventive Examples and Comparative Examples are applied over a surface of a substrate including the word "Translucent" repeatedly displayed thereon. Increases in the transparency provide increases in the visibility of the word "Translucent" through the composition. As shown in FIG. 2, the Comparative Examples are opaque or cloudy, whereas, in contrast, the Inventive Examples are transparent.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition in the form of a water-in-oil emulsion comprising:
   an aqueous phase, the aqueous phase at a concentration, by weight, of about 50% to about 90%, based upon weight of the composition, wherein the aqueous phase includes at least one amphiphilic compound selected from the group consisting of urea, sodium 5-oxo-2-pyrrolidinecarboxylate (sodium PCA), hydroxyethyl urea, nicotinamide, sodium citrate, ascorbic acid, or combinations thereof, wherein the at least one amphiphilic compound is at a concentration, by weight, of about 2% to about 50%, based upon weight of the composition; and
   an oil phase comprising at least one water-in-oil emulsifier, the water-in-oil emulsifier being an emulsifying linear silicone at a concentration, by weight, of about 1% to about 25%, based upon weight of the composition;
   wherein the emulsifying linear silicone is dimethicone (and) PEG/PPG-18/18 dimethicone at a concentration, by weight, of about 3% to about 10%, based upon weight of the composition and,
   wherein the water-in-oil emulsion is a transparent or translucent composition.

2. The cosmetic composition of claim 1, wherein the dimethicone (and) PEG/PPG-18/18 dimethicone is at a concentration, by weight, of about 5% to about 8%, based upon weight of the composition.

3. The cosmetic composition of claim 1, the aqueous phase comprising at least one active compound, the at least one active compound being at a concentration, by weight, of about 0.001% to about 30%, based upon weight of the composition.

4. The cosmetic composition of claim 1, wherein the at least one amphiphilic compound is nicotinamide.

5. The cosmetic composition of claim 1, wherein nicotinamide is at a concentration, by weight, of about 2% to about 20%, based upon weight of the composition.

6. The cosmetic composition of claim 1, wherein nicotinamide is at a concentration, by weight, of one of about 4% to about 12%, 15%, and 20%, based upon weight of the composition.

7. The cosmetic composition of claim 1, comprising at least one silicone oil, the at least one silicon oil chosen from co-emulsifiers selected from the group consisting of lauryl PEG-9 polydimethylsiloxyethyl dimethicone, PEG-10 dimethicone, and PEG-9 polydimethylsiloxyethyl dimethicone (and) PEG-9, dimethicone, a mixture of dimethicone and dimethiconol, and combinations of these.

* * * * *